United States Patent [19]

Bonaldi et al.

[11] 4,316,848
[45] Feb. 23, 1982

[54] PROCESS FOR THE PURIFICATION OF URSODEOXYCHOLIC ACID

[75] Inventors: Antonio Bonaldi, Schilpario; Egidio Molinari, Erba, both of Italy

[73] Assignee: Blasinachim S.p.A, Milan, Italy

[21] Appl. No.: 167,468

[22] Filed: Jul. 11, 1980

[30] Foreign Application Priority Data

Jul. 12, 1979 [IT] Italy .............................. 24316 A/79

[51] Int. Cl.$^3$ .............................................. C07J 9/00
[52] U.S. Cl. ................................................. 260/397.1
[58] Field of Search ..................................... 260/397.1

[56] References Cited

U.S. PATENT DOCUMENTS 3,671,555  6/1972  Teichmuller et al. ............ 260/397.4
3,833,620  9/1974  Saltzman ........................... 260/397.1
3,919,266  11/1975  Saltzman .......................... 260/397.1

OTHER PUBLICATIONS

Hisatsune et al., "Chem. Pharm. Bull.", No. 26, (9), (1978), pp. 2922–2923.
Karlaganis et al., "Clin. Chem. Act.", (1979), 92, pp. 19–26.
Chemical Abstracts 87, Pars. 85,166c, (1977).
Chemical Abstracts 87, Pars. 168,277r, (1977).
Chemical Abstracts 88, Pars. 148,367n, (1978).
Anal. Biochem., (1978), 85 No. 1, pp. 197/208.

*Primary Examiner*—Elbert L. Roberts
*Attorney, Agent, or Firm*—Stevens, Davis, Miller & Mosher

[57] ABSTRACT

A mixture of ursodeoxycholic acid and of chenodeoxycholic acid as well as of their salts and esters is reacted with a silylating agent in a suitable anhydrous organic solvent; the corresponding silyl-derivatives thus obtained are separated by crystallization and pure ursodeoxycholic acid is recovered from the corresponding silyl-derivatives in the usual manner.

5 Claims, No Drawings

PROCESS FOR THE PURIFICATION OF URSODEOXYCHOLIC ACID

This invention relates to the purification of crude ursodeoxycholic acid (UDCA).

More particularly, this invention relates to a process for the manufacture of UDCA practically free from chenodeoxycholic acid (CDCA).

Furthermore, this invention is directed to the preparation of some new derivatives of UDCA that are useful for the purification of UDCA.

Since long time UDCA is used in the human medicine as a colagogue but only very recently it has been discovered that it is endowed with gallstone dissolving activity. UDCA is epimeric with CDCA in respect to the hydroxyl group at $C_7$.

UDCA may be prepared from CDCA by steric conversion of the hydroxyl group at $C_7$, after having protected the hydroxyl group at $C_3$ in a selective way. At this purpose the 7-α-hydroxyl group is oxidized to the corresponding 7-keto group and then the 7-keto group is reduced as to obtain the 7-β-hydroxyl group.

Unfortunately, no reducing agent is able to reduce quantitatively the 7-keto group to the 7-β-hydroxyl group. In practice UDCA thus obtained contains from 10 to 40% of CDCA.

The separation of UDCA from CDCA by crystallization or by fractionated crystallization or by preparative chromatography are of no use on industrial scale.

It has been now found that some new silyl-derivatives of UDCA possess different solubility rates in many organic solvents with respect to the corresponding derivatives of CDCA so that it is possible to separate UDCA from CDCA and to prepare UDCA substantially free from CDCA on industrial scale.

The new silyl-derivatives of this invention have the following general formula:

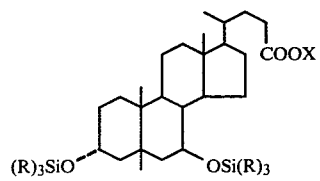

Wherein
X is selected from the group consisting of non substituted and substituted alkyl radical having from 1 to 6 carbon atoms, aryl and arylalkyl radical, $Si(R_3)$, $N^+H(R')_3$;

R is selected from the group consisting of linear and branched alkyl radical having from 1 to 5 carbon atoms; R' is selected from the group consisting of hydrogen and lower alkyl group.

The new silyl-derivative of this invention may be prepared by reacting a mixture of UDCA and CDCA as well as of their salts and esters, with a silylating agent in a suitable anhydrous organic solvent.

As silylating agents may be used bis- and tris-alkyl-silyl-halogenides, bis-trialkyl-silyl-ureas, bis-alkyl-silyl-arylamides, hexaalkyldisilazanes and mixture thereof. Preferably the alkyl-groups of the above mentioned silylating agents have no more than 5 carbon atoms.

Suitable organic solvents for carrying out the silylation are the aromatic hydrocarbons such as benzene and toluene, the nitriles, the esters, the amides and their derivatives on condition that they are deprived of any reactive hydrogen atom.

Further suitable solvents are the chlorinated aliphatic hydrocarbons like chloroform, methylene chloride and carbon tetrachloride; aliphatic and aromatic ketones such as acetone, methylisobutylketone, acetophenone, ciclic-esters such as dioxane and tetrahydrofurane.

Either the bis- or the tris-silylderivatives of UDCA of this invention precipitate from the reaction mixture by cooling and are collected by filtration.

When X is $Si(R_3)$ and $NH^+(R')_3$ the precipitate is treated with acids to obtain pure UDCA substantially free from CDCA. When X is alkyl, aryl and arylalkyl radical, the precipitate is treated with alkali to obtain the product wherein X is H and the bis-silyl derivative thus obtained is treated with acids to obtain pure UDCA substantially free from CDCA. CDCA is recovered from the mother liquors almost quantitatively and may be recycled.

The following examples are intended only to illustrate but not to limit this invention.

EXAMPLE 1

60 g of UDCA containing about the 15% of CDCA are suspended in 300 ml of acetonitrile.

The suspension is added, under stirring, with 90 g of bistrimethylsilyl-urea (BSU) and it is heated slowly up to the boiling; after two hours it is cooled to 0° C., the precipitate is collected by filtration and crystallized from acetonitrile in the presence of 10% of BSU.

Yield, 75 g of trimethylsilyl derivative of UDCA, m.p. 125° C.; $[\alpha]_D + 49.5°$ (1% dioxane).

50 g of the trimethylsilyl derivative of UDCA are added to a 5% solution of hydrochloric acid and the suspension thus obtained is warmed at 40°–50° C. for ten minutes. After cooling, the precipitate is collected by filtration, washed till no more acid is present in the washing water, dried and recrystallized from ethyl acetate.

Yield, 46.1 g; m.p. 204° C.; CDCA content: less than 0.1%. The acetonitrile mother liquors are concentrated by evaporation of the solvent and added with diluted hydrochloric acid.

The precipitate is collected by filtration, washed and dried.

Yield, 9 g of a mixture, containing 60 parts of UDCA and 40 parts of CDCA, which is recycled.

EXAMPLE 2

60 g of a mixture of methyl-ursodeoxycholate and of methyl-chenodeoxycholate are dissolved in 300 ml of N,N-dimethylformamide (DMF) and are added, undeer stirring, with 80 g of bistrimethyl-silyl-acetamide; the mixture is heated slowly up to 100° C. and it is maintained at this temperature for 2 hours.

After cooling at 0° C., the silyl-derivative of methyl ursodeoxycholate is collected by filtration, washed with DMF and dried: m.p. 115° C.; $[\alpha]_D + 48.6$ (1% dioxane).

The 3,7-disilyl-derivative of methyl-ursodeoxycholate thus prepared is refluxed in an aqueous solution of sodium hydroxyde.

When the hydrolysis of the ester is complete, the product is treated with acid in order to remove the silyl-groups and recovered by precipitation and filtration. The solid product is washed and crystallized from ethyl acetate.

EXAMPLE 3

50 g of UDCA containing about the 20% of CDCA are suspended in 400 ml of ethyl acetate and added with 25 ml of trimethylchlorosilane and 25 ml of hexamethyldisinazane. The mixture is heated at 80° C. for 1 hour, then it is cooled at 0° C. The precipitate, consisting of trisilyl-derivative of UDCA undergoes acid hydrolysis as disclosed in the example 1.

EXAMPLE 4

39.2 g of a mixture of UDCA and of CDCA are dissolved in 400 ml of dimethylformamide.

The solution is added with 32 g of hexamethyldisilazane at room temperature and maintained under stirring for 2 hours. The precipitate is collected, washed with dimethylformamide and processed as disclosed in the example 1.

EXAMPLE 5

19.6 g of a mixture of UDCA and of CDCA are dissolved in 100 ml of acetonitrile. In this solution it is bubbled ammonia gas up to saturation and then 10 g of hexamethyldisilazane are added.

The solution thus obtained is kept under stirring for 5 hours at 20° C. to 30° C.

The precipitate is collected, washed with acetonitrile and processed as disclosed in the example 1. UDCA substantially pure is obtained.

EXAMPLE 6

39.2 g of UDCA with a 20% content of CDCA are dissolved in 400 ml of ethyl acetate. After having added 10.1 g of triethylamine and, thereafter, 30.5 g of bis-trimethylsilylacetamide, the solution is maintained under stirring at 20° C. to 30° C. for 5 hours. After cooling the precipitate is collected by filtration, washed with ethyl acetate and processed as disclosed in the example 1. Pure UDCA is obtained.

EXAMPLE 7

20 g of a mixture containing about 50% of UDCA and CDCA are dissolved in 50 ml of dimethylformamide; 20 g of bistrimethylsilyl-urea are added and the solution is kept at 100° C. for 1 hour. Then the solution is cooled, the precipitate is collected by filtration and washed with dimethylformamide. Yield, 9 g of UDCA containing about 5% of UDCA.

This mixture is redissolved in dimethylformamide; the solution is added with 2 g of bistrimethylsilyl-urea, heated up to 100° C. and kept at this temperature for 1 hour. After cooling the precipitate is collected by filtration, washed with dimethylformamide and dried. The trisilyl-derivative of UDCA highly pure so obtained undergoes acid hydrolysis as disclosed in example 1.

What we claim is:

1. A method for the separation of a mixture selected from the group consisting of: (i) ursodeoxycholic and chenodeoxycholic acids, (ii) a salt of each of said acids, and (iii) an ester of each of said acids, into the components of said mixture, by:
   (a) reacting said mixture with a silylating agent in a suitable anhydrous organic solvent, whereby the silyl-derivatives of said components are formed, and
   (b) separating said derivatives by crystallization.

2. Method according to claim 1 characterized in that the silylating agent is selected from the group consisting of hexamethyldisilazane, trimethylchlorosilane, bis-trimethylsilylurea, bistrimethylsilylacetamide and mixture thereof.

3. Method according to claim 1 or 2 characterized in that the organic solvent is selected from the group consisting of acetonitrile, dimethylformamide and ethylacetate.

4. New sylil-derivatives having the following general formula:

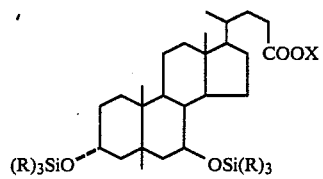

wherein:
X is selected from the group consisting of Si(R)$_3$, and N+H(R')$_3$,
R is selected from the group consisting of linear and branched alkyl radicals having from 1 to 5 carbon atoms;
R' is selected from the group consisting of hydrogen and a lower alkyl group.

5. 3, α, 7β, 24-tris-trimethylsilyl derivative of ursodeoxycholic acid.

* * * * *